United States Patent [19]
Kohlpaintner et al.

[11] Patent Number: 5,631,393
[45] Date of Patent: May 20, 1997

[54] PALLADIUM CATALYSTS CONTAINING SULFONATED BISPHOSPHINES AS LIGANDS, PROCESS FOR THEIR PREPARATION AND THEIR USE IN CARBONYLATION REACTIONS

[75] Inventors: Christian Kohlpaintner, Kelkheim; Matthias Beller, Niedernhausen, both of Germany

[73] Assignee: Hoechst Aktiengesellschaft, Frankfurt, Germany

[21] Appl. No.: 433,315

[22] Filed: May 2, 1995

[30] Foreign Application Priority Data

May 4, 1994 [DE] Germany .................. 44 15 682.0

[51] Int. Cl.$^6$ .................. C07F 9/02; C07F 15/00
[52] U.S. Cl. .................. 556/17; 556/21; 556/136; 502/162; 562/35; 562/406
[58] Field of Search .................. 556/17, 21, 136; 502/162; 562/35, 406

[56] References Cited

U.S. PATENT DOCUMENTS 5,347,045  9/1994  Herrmann et al. .................. 562/35

FOREIGN PATENT DOCUMENTS 0544455  6/1993  European Pat. Off. .
0571819  12/1993  European Pat. Off. .

*Primary Examiner*—Porfirio Nazario-Gonzalez
*Attorney, Agent, or Firm*—Connolly & Hutz

[57] ABSTRACT

The invention relates to palladium compounds containing as ligands compounds of the formula (I)

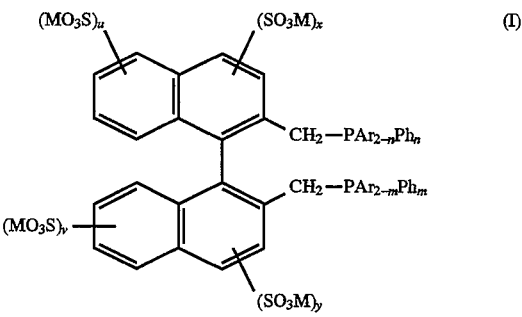

where Ar is $C_6H_4SO_3M$, M is hydrogen, ammonium, a monovalent metal or one equivalent of a polyvalent metal and Ph is the phenyl radical and n, m are zero, 1 or 2 and x, y, u, v are zero, 1 or 2.

18 Claims, No Drawings

PALLADIUM CATALYSTS CONTAINING SULFONATED BISPHOSPHINES AS LIGANDS, PROCESS FOR THEIR PREPARATION AND THEIR USE IN CARBONYLATION REACTIONS

DESCRIPTION

The present invention relates to novel BINAS-palladium catalysts, a process for their preparation and their use in carbonylation reactions.

For the purposes of the present invention, BINAS are phosphines which can be obtained by sulfonation of 2,2'-bis(diphenylphosphinomethyl)-1,1'-binaphthalene (EP 571 819).

Such compounds are used as ligands in rhodium complexes which are used as catalysts in hydroformylation reactions (EP 571 819).

Carbonylation reactions play an important role in the synthesis of organic compounds and a series of catalysts have been described for this reaction (H.M. Colquhoun, D.J. Thompson, M.V. Twigg, Carbonylation, Plenum Press 1991, New York). In view of the multiplicity of use opportunities for this reaction, there is a need for new catalysts, on the one hand to supplement and expand the range of their application opportunities and, on the other hand, to be able to carry out certain reactions particularly favorably.

This object is achieved by palladium compounds containing as ligands compounds of the formula (I)

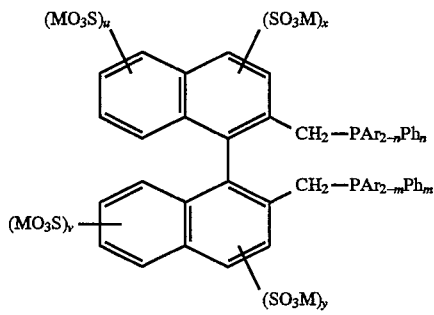

where Ar is $C_6H_4SO_3M$, M is hydrogen, ammonium, a monovalent metal or one equivalent of a polyvalent metal and Ph is the phenyl radical and n, m are zero, 1 or 2 and x, y, u, v are zero, 1 or 2.

Very well suited compounds are those in which n, m are zero and x, y, u, v are zero or 1.

The palladium compounds of the invention containing ligands of the formula (I) can be prepared by 2 methods.

One possibility is the direct synthesis from palladium salts of organic or inorganic acids by reaction with BINAS.

Salts which are well suited for this purpose are, for example, palladium acetate or palladium chloride.

Furthermore, the palladium compounds containing ligands of the formula (I) can also be obtained by exchange reactions from other palladium complexes such as, for example, $PdCl_2$ $(PPh_3)_2$, $PdCl_2$dppe (dppe=1,2-bis(diphenyl-phosphino) ethane) or $Pd(PPh_3)_4$ with BINAS.

The compounds of the invention having the formula (I) are suitable for carbonylation reactions, in particular for carbonylation reactions in which the water-solubility of the catalyst is of importance.

The preparation of arylacetic acid derivatives by carbonylation of arylmethyl halides using a water-soluble metal complex as catalyst in a two-phase system is the subject matter of an application filed on the same day, Ser. No. 08/433,703 as the present invention.

The catalysts of the invention are particularly well suited for such a reaction. It is found that when a catalyst of the invention is used in this reaction it is not necessary to add base. On the one hand, this avoids formation of salt, and on the other hand the product selectivity is thereby increased again significantly, since the hydrolysis of the arylmethyl halide to the corresponding alcohol occurring in an alkaline medium does not occur without addition of base.

However, the catalyst of the invention is also well suited for other carbonylation reactions, for example the carbonylation of alkynes, of organolithium or Grignard reagents and the carbonylation of ether compounds.

Olefins can also be hydrocarboxylated in a simple manner using these catalysts. The catalysts of the invention can be recycled without problems.

The following examples illustrate the invention without limiting it to them.

EXAMPLE 1

Preparation of the Catalyst from Palladium Salts by Direct Synthesis 500 mg (2.2 mmol) of $Pd(OAc)_2$ are dissolved in 40 ml of o-xylene by heating. 22.3 g of a solution of BINAS in water (100 mmol of BINAS/kg of solution) and 20 ml of water are added thereto. The reaction mixture is subsequently stirred for three hours at room temperature. When the organic phase is completely decolorized, the aqueous phase is separated off, chromatographed over a Sephadex gel and evaporated to dryness.

Yield: 3.46 g.

$^{31}$P-NMR ($D_2O$): δ=20.3 ppm (s).

EXAMPLE 2

Preparation of the Catalyst by an Exchange Reaction with $PdCl_2(PPh_3)_2$ 5.0 g (7.1 mmol) of $PdCl_2(PPh_3)_2$ are dissolved in 150 ml of toluene and 75 g of a solution of BINAS in water (100 mmol of BINAS/kg of solution) are added so as to form a lower layer. The mixture is vigorously stirred at room temperature until the organic phase is completely decolorized. The aqueous phase is subsequently separated off and evaporated to dryness.

Yield: 15.43 g.

$^{31}$P-NMR ($D_2O$): δ=22.1 ppm (s).

EXAMPLE 3

Carbonylation of Benzyl Chloride 2.53 g (20 mmol) of benzyl chloride and 45 mg (0.2 mmol) of $Pd(OAc)_2$ are dissolved in 30 ml of toluene and admixed with 8 ml of an aqueous solution of BINAS (100 mmol/kg of solution). A further 30 ml of water are subsequently added. The two-phase mixture is stirred for a period of 20 hours in a 200 ml Hastelloy autoclave at a temperature of 70° C. and a CO pressure of 20 bar. At the end of the reaction time, the autoclave is cooled, vented and the reaction mixture is placed in a separating funnel. The supernatant organic phase is separated off and evaporated to dryness. This gives 2.52 g of phenylacetic acid as a white powder (92.5% of theory).

Elemental Analysis:

Calc.: C 70.58, H 5.92, O 23.50.

Found: C 70.30, H 5.80, O 23.90 (1st determination).

Found: C 70.60, H 6.00, O 23.40 (2nd determination).

EXAMPLE 4

Recycling of the Catalyst

The aqueous catalyst solution separated off in Example 1 is adjusted to a pH of 7 prior to the commencement of the reaction and is stirred together with 2.53 g (20 mmol) of benzyl chloride, dissolved in 30 ml of toluene, in a 200 ml Hastelloy autoclave for 20 hours at 70° C. under a CO pressure of 20 bar. At the end of the reaction, the organic phase is separated off and evaporated to dryness on a rotary evaporator. This gives 2.45 g of phenylacetic acid as a white powder (89.9% of theory).

EXAMPLE 5

The procedure of Example 4 is repeated, reusing the aqueous catalyst solution separated off therein, after adjustment to pH 7, for the carbonylation of benzyl chloride.

Yield: 2.38 g (87.4% of theory) of phenylacetic acid.

EXAMPLE 6

Hydrocarboxylation Reaction 56.7 mg (0.32 mmol) of $PdCl_2$ and 94.1 mg (0.7 mmol) of $CuCl_2$ together with 1.04 g (10 mmol) of styrene are dissolved in 50 ml of toluene and admixed with 5 ml of a BINAS solution (100 mmol of BINAS/kg of solution) and 10 ml of water. The mixture is placed in a 200 ml Hastelloy autoclave and stirred for 19 hours at a temperature of 50° C. and a CO pressure of 40 bar. The autoclave is subsequently cooled and vented. The organic phase is separated off and evaporated to dryness. Residue: 0.95 g (63% of theory). After recrystallization: 0.84 g (56% of theory) of phenyl-propionic acid.

We claim:

1. A palladium compound containing as ligands compounds of the formula (I)

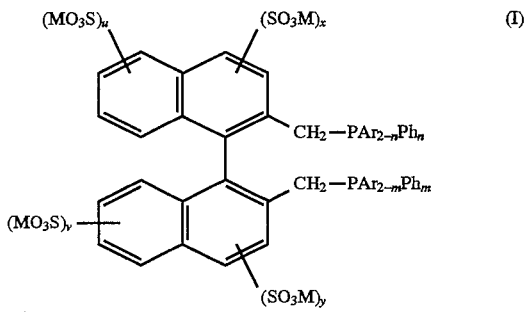

where Ar is $C_6H_4SO_3M$, M is hydrogen, ammonium, a monovalent metal or one equivalent of a polyvalent metal and Ph is the phenyl radical and n, m are zero, 1 or 2 and x, y, u, v are zero, 1 or 2.

2. A compound as claimed in claim 1, wherein n and m are zero and x, y, u, v are zero or 1.

3. A process for preparing a palladium compound as claimed in claim 1, which comprises reacting palladium salts of organic or inorganic acids with compounds of the formula (I).

4. The process as claimed in claim 3, wherein $PdCl_2$ or $Pd(OAc)_2$ is used as palladium salt.

5. The process for preparing a palladium compound as claimed in claim 1, wherein palladium complexes with compounds of the formula (I) are used.

6. The process as claimed in claim 5, wherein $PdCl_2(PPh_3)_2$ or $Pd(PPh_3)_4$ is used as palladium complex.

7. The compound as claimed in claim 1, wherein n is zero.

8. The compound as claimed in claim 1, wherein m is zero.

9. The compound as claimed in claim 7, wherein m is zero.

10. A catalyst for carbonylation reactions comprising a palladium compound containing as ligands compounds of the formula (I)

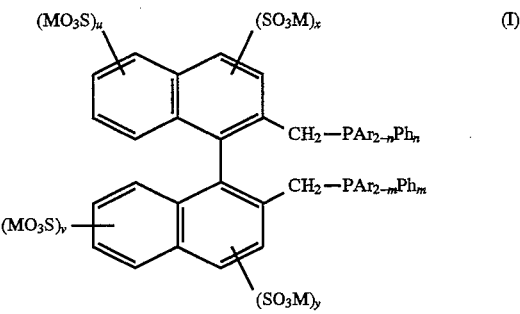

where Ar is $C_6H_4SO_3M$, M is hydrogen, ammonium, a monovalent metal or one equivalent of a polyvalent metal and Ph is the phenyl radical and n, m are zero, 1 or 2 and x, y, u, v are zero, 1 or 2.

11. The catalyst as claimed in claim 10, wherein n is zero.

12. The catalyst as claimed in claim 10, wherein m is zero.

13. The catalyst as claimed in claim 11, wherein m is zero.

14. The catalyst as claimed in claim 13, wherein x, y, u, v are zero or 1.

15. A process for preparing carboxylic acids comprising carbonylating olefins with the catalyst as claimed in claim 10, thereby producing a carboxylic acid.

16. A process for preparing carboxylic acids comprising carbonylating organo lithium reagents with the catalyst as claimed in claim 10, thereby producing a carboxylic acid.

17. A process for preparing carboxylic acids comprising carbonylating Grignard reagents with the catalyst as claimed in claim 10, thereby producing a carboxylic acid.

18. A process for preparing carboxylic acids comprising carbonylating ether compounds with the catalyst as claimed in claim 10, thereby producing a carboxylic acid.

* * * * *